United States Patent [19]

Mouneimne et al.

[11] Patent Number: 5,236,835
[45] Date of Patent: Aug. 17, 1993

[54] ELECTRO INSERTION OF PROTEINS INTO RED CELL MEMBRANES

[75] Inventors: Youssef Mouneimne, College Station; Pierre-Francois Tosi, Bryan; Yves-Claude Nicolau, College Station, all of Tex.

[73] Assignee: Hapgood, C.V., Oldwick, N.J.

[21] Appl. No.: 809,049

[22] Filed: Dec. 17, 1991

Related U.S. Application Data

[63] Continuation of Ser. No. 407,664, Sep. 19, 1989, abandoned, which is a continuation-in-part of Ser. No. 254,550, Oct. 5, 1988, abandoned.

[51] Int. Cl.$^5$ ............... C12N 13/00; A61K 37/10
[52] U.S. Cl. ............... 435/173.6; 514/8
[58] Field of Search ............... 435/173; 514/8

[56] References Cited

FOREIGN PATENT DOCUMENTS 0101341 2/1984 European Pat. Off.
0298280 1/1989 European Pat. Off.
2374045 7/1978 France.

OTHER PUBLICATIONS

Hofmann et al. (Dec. 1986) IEEE Eng. in Med. & Biol. pp. 6-23.
Zimmerman et al. (1982) J. Memb. Biol., 165-182.
Bates et al. (1987) in "Cell Fusion" pp. 367-395, A. E. Sowers, ed., Plenum Press.
Biological Abstracts, vol. 80, No. 1, 1985, abstract No. 622, E. H. Serpersu et al.; Reversibel and irreversible modification of erythrocyte membrane permeability by electric field.
Chemical Abstracts, vol. 107, No. 7, Aug. 17, 1987, p. 30 abstract No. 51519m Jastreboff et al. Use of electroporation to study the cytotoxic effects of fluorodeoxyuridylate in intact cells.
Chemical Abstracts, vol. 110, No. 7 Feb. 13, 1987, p. 356 Abstract No. 54113x, J. G. Bliss et al. Electroporation: the population distribution of macromolecular uptake and shape changes in red blood cells following a single 50 mus square wave pulse.
Biochemical and Biophysical Research Communications, vol. 159, No. 1, Feb. 28, 1989, pp. 34-40, Y. Mouneimne et al. Electro-insertion of xeno-glycophorin into the red blood cell membrane.
Inhibition of complement activation on the surface of cells after incorporation of Decay-Accelerating Factor (DAF) into their membranes M. Edward Medof et al. J. Exp Med The Rockefeller University Press vol. 160 Nov. 1984 pp. 1558-1578.
Deficiency of the Homologous Restriction Factor in Paroxysmal Nocturnal Hemoglobinuria Journal of Experimental Medicine vol. 165 Feb. 1987 pp. 572-577 Leora S. Zalman et al.
Incorporation and Asymmetric Orientation of Glycophorin in Reconstituted Protein Protein-Containing Vesicles R. C. MacDonald Eur. J. Biochem. 86, pp. 539-546 (1978).

Primary Examiner—David M. Naff
Assistant Examiner—Jon P. Weber

[57] ABSTRACT

A method of incorporating human CD4 or glycophorin into a red blood cell membrane is provided comprising exposing the red blood cell to an electric field while the cell is suspended in an electro-insertion medium in the presence of a buffered solution (suspension) of the proteins. These proteins bear a hydrophobic membrane spanning sequence. The resultant cell of the electro-insertion is then contacted with a resealing medium.

16 Claims, 7 Drawing Sheets

OTHER PUBLICATIONS

Inhibition of antibody-Dependent Lymphocyte Cytotoxicity by Homologous striction factor incorporated Into Target Cell Membranes Leora S. Zalman J. Exp. Med. 166 pp. 947–955 (1987).

Reconstitution of Membrane proteins The Journal of Biological Chemistry, vol. 253, pp. 18500–18506 (1988) Scotto et al.

Cell Fusion, A. E. Sowers, ed. Plenum Press, New York 1987 pp. 367–395 Electrofusion Principles and Applications George W. Bates et al. Chapter 17.

Electronic Genetic-Physical and Biological Aspects of Cellular Electromanipulation Electromanipulation Gunter A. Hofmann Engineering in Medicine and Biology Magazine pp. 6–23.

The Electrofusion Mechanism in Erythrocyte Ghosts chapter 18 A. E. Sowers Cell Fusion 1987.

Electric Field-Induced Cell-to-Cell Fusion C. Zimmermann; Membrane Biology pp. 165–182.

Direct Experimental Evidence of the Vectorial Character of the Interaction Between Electric Pulses and Cells in Cell Electrofusion J. Teissie Biochimica et Biophysica Acta 775 (1984) pp. 446–449.

Reversible and irreversible modification of erythrocyte membrane permeability by electic field Engin H. Serpersu et al. Biochimica et Biophysica Acta 812 pp. 779–785.

Stochastic Model for Electric Field-Induced Membrane Pores Electroporation I. P. Sugar et al. Biophysical Chemistry 19 (1984) pp. 211–225.

Formation and properties of aqueous leaks induced in human crythrocytes by electrical breakdown K. Schwister et al Biochimica et Biophysica Acta 816 pp. 332–349.

Effects of External Electrical Fields on Cell Membranes U. Zimmermann et al. Bioelectrochemistry and Bioenergetics 3, pp. 58–83 (1976).

ELECTRO INSERTION OF PROTEINS INTO RED CELL MEMBRANES

CROSS-REFERENCE TO RELATED APPLICATION

This application is a continuation of application Ser. No. 407,664, filed Sep. 19, 1989, now abandoned, which is a continuation in part of Ser. No. 254,550, filed Oct. 5, 1988, now abandoned.

BACKGROUND OF THE INVENTION

1. Field of the Invention

The present invention concerns a method for incorporating a protein into an animal cell membrane by exposing the cell to electric field pulses.

2. Background Information

Electroporation or electrofusion is described by Zimmerman, Neumann, Tsong, Kinosita, Tessie, Deutike, etc., *Cell Fusion*, ed., A. E. Sowers, Plenum Press, New York 1987; *Electronic Genetic-Physical and Biological Aspect of Cellular Electromanipulation*, Gunter A. Hofmann and Glen A. Evans, IEEE Eng. in Med. and Biol. Magazine, December 1986, p. 6, "Dielectric Breakdown-Fusion/Electroporation".

The following papers described spontaneous insertion of a variety of proteins into cell membranes: Medof et al, "Inhibition of Complement Activation of the Surface of Cells After Incorporation of Decay-Accelerating Factor (DAF) Into their Membranes", *J. Exp. Med.*, 160, 1558-1578 (1984); Zalman et al, "Deficiency of the Homologous Restriction Factor in Paroxysmal Nocturnal Hemoglobinuria", *Journal of Exp. Med.*, 165, 572-577 (1987); "Incorporation and Assymmetric Orientation of Glycophorin in Reconstituted Protein-Containing Vesicles", *Eur. J. Biochem.*, 86, 539-546 (1978); Zalman et al, "Inhibition of Antibody-Dependent Lymphocyte Cytotoxicity by Homologous Restriction Factor Incorporated Into Target Cell Membranes", *J. Exp. Med.*, 166, 947-955 (1987); Scotto et al, "Reconstitution of Membrane Proteins", *The Journal of Biological Chemistry*, 263, 18500-18506, (1988). These papers, however, do not concern electro-insertion.

SUMMARY OF THE INVENTION

The present invention concerns a method of incorporating a protein into a cell membrane (e.g., an animal cell membrane) comprising exposing a cell to an electric field while the cell is suspended in an electro-insertion medium in the presence of a buffered solution (suspension) of the protein(s) to be inserted, the protein bearing a hydrophobic membrane spanning sequence and then contacting the resultant cell with a resealing medium.

DETAILED DESCRIPTION OF THE INVENTION

Figure 1B:
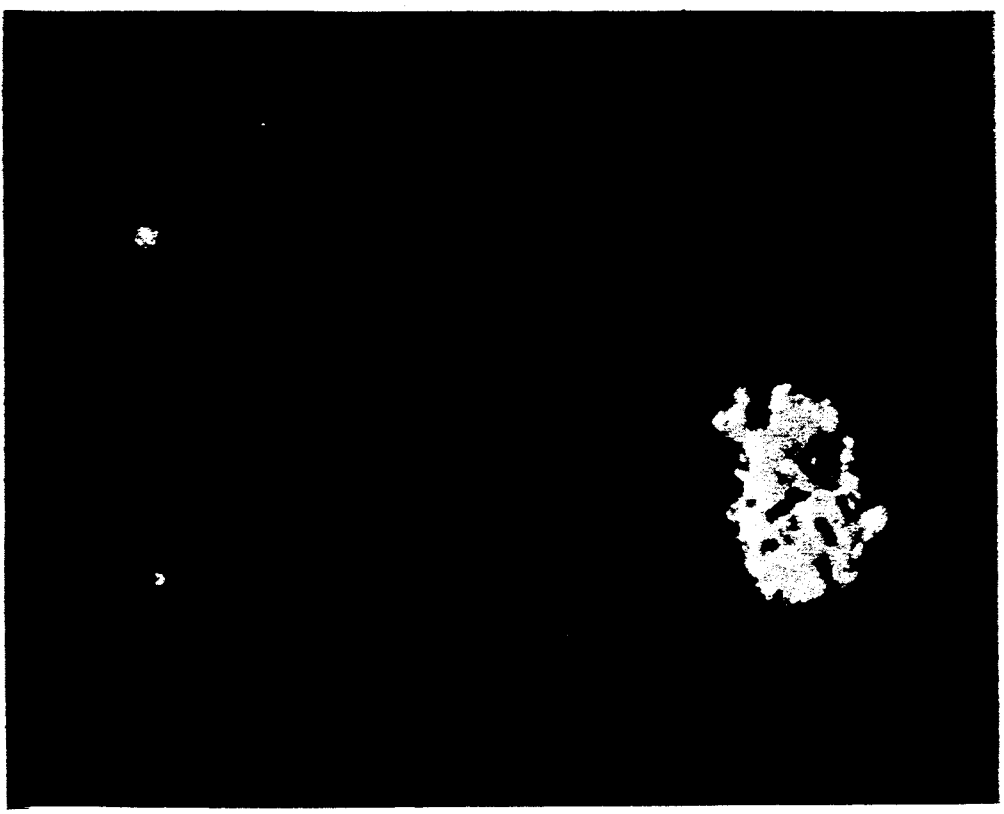
FIG. 1b is another photograph depicting aggregation of murine red blood cells bearing human glycophorin shown by fluorescence microscopy.

The present invention concerns the incorporation of a protein bearing a hydrophobic membrane spanning sequence through a cell membrane by exposing the cell to an electric field, preferably one or more electric field pulses, while the cell is suspended in an electro-insertion medium and thereafter contacting the resultant cell with a resealing medium.

It is preferred to carry out the inventive method at 2° C. to 39° C., with 37° C. being particularly preferred.

It is preferred to carry out the inventive method up to and including resealing in 1 to 4 hours, with 3 hours being particularly preferred.

Cells suspended in a liquid can be modeled as a structure consisting of a non-conducting membrane with aqueous solutions on both sides. Exposure to an electric field leads to charge separation in the membrane similar to the charge separation in the dielectric layers of an electrical capacitor. This results in a transmembrane potential difference. Opposite electrical charges on the membrane attract each other, exerting a pressure on the membrane which can induce membrane thinning. At a critical potential difference (field strength), localized breakdown of the membrane occurs and pores are formed, allowing a flow of medium or cytoplasm. Removal of the field can lead to healing (closing) of the pores, provided that the field strength and pulse width are not excessive.

The present invention is applicable to cells generally because it deals with the lipid membrane of cells, taking into account a possible need for special conditions for certain types of cells. Non-limiting examples of cells for use in the present invention include red blood cells, lymphocytes, monocytes, mammalian culture cells of all types, fibroblasts, hepatocytes, endothelial cells, neurons and macrophages, just to mention a few. The invention is also applicable for plant cells and microorganisms, e.g., bacteria and yeast.

Any cell can be subjected to electro insertion according to the invention with, if needed, special electrical, chemical and/or biological conditions, i.e., human and monkey cell lines (Hela, CVI, Vero), mouse and hamster cell lines (N1H3T3, CHO), insect cells, yeast, bacteria and plant cells, just to name a few.

The cell is preferably an animal cell, and most preferably a warm blooded animal. The cell can be from a human or another warm blooded animal, e.g., cow, cat, rabbit, monkey, mouse, goat, sheep or horse. Preferably the cell is found in the bloodstream. More preferably the cell is an erythrocyte. The cell could also be a human lymphoma T cell or culture cells, e.g., nucleated animal cells in culture for example, CEM cells.

Any protein bearing a hydrophobic membrane spanning sequence can be used in the invention. Besides glycophorin and CD4, CD2, CD3, MHC Class I and II, LDL receptor, insulin receptor, different hormone receptors or any genetically engineered soluble protein bearing a specific trans-membrane hydrophobic sequence can be employed. The preferred proteins for insertion are human glycophorin and human CD4.

The electro-insertion occurs according to the empiric law $$V = V_o + 1.5 \, RE \cos(\theta),$$

where V is the resultant membrane potential and $V_o$ is the natural membrane potential. R is the cell radius, E is the field strength, and $\theta$ is the angle between a given membrane site and the field direction.

Figure 8:
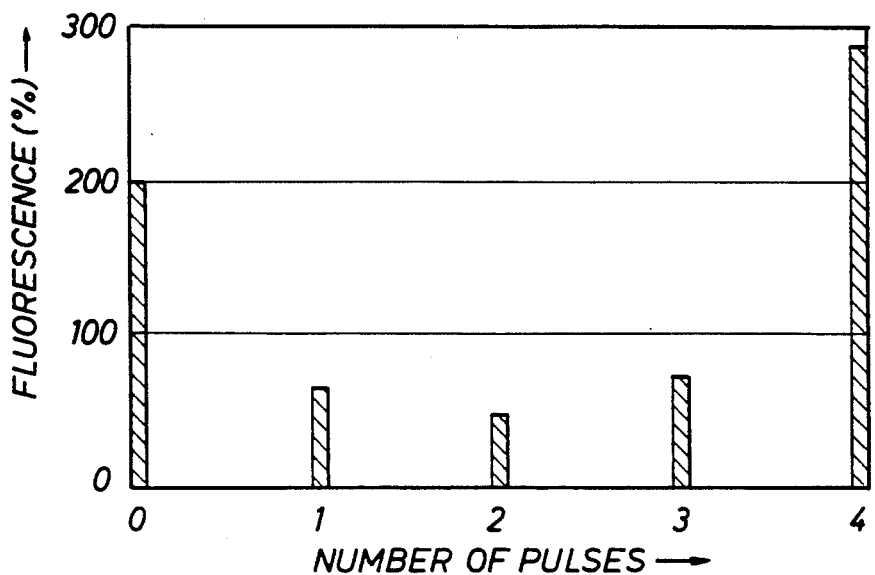
FIG. 8 is a series of bar graphs which show the amount of inserted protein molecules per cell (represented as relative fluorescence intensity), detected by flow cytometry, depends on the number of applied electrical pulses. The system employed was murine RBC-glycophorin.

Reduction of the membrane potential by pretreating the red blood cells with ionophor A23187 leads to a 85% decrease of insertion efficiency of glycophorin into rabbit red blood cells. Obviously, with no external field, minimum inserted molecules per cell are obtained. Application of four electrical pulses produces a high insertion. FIG. 8 shows the fluorescence intensity relative to the insertion of human glycophorin into murine red blood cell, with no external field and using up to four electrical pulses.

The maximum number of pulses for use in the invention is limited only by the behavior of the cell under the multiple pulses and the time limiting biological and chemical conditions of the procedure. The maximum could be 100 pulses, but there is no need to employ such number of pulses as long as a maximum efficiency for a limited number of pulses is achieved. The aim of the use of multiple pulses is to increase the probability of the exposure of cells to the electric field.

In order to achieve intact cells any pulse height equal to or below the critical field for electroporation can be used, but the insertion decreases with decreased height value. Pulses equal or higher than the critical field are also efficient, but the cells swell or lyse. The same occurs for the duration, lower pulses (i.e. <400 $\mu$s), but they are also good but less efficient. Longer pulses may be more efficient, but they cause heat increase and damage, and depending on the electrical field intensity, up to second(s) pulses can be used. In general, the applied field and the duration of the pulse are inversely proportional and cell type dependent. The interval between pulses can be microseconds to minutes; the only limitation is the heat dissipation of the electric chamber and the recovery of the cells after each pulse.

The pulse shape need not be square and any pulse shape is efficient as long as the required energy (E,T) is provided. An exponential decay, sawtooth, or even alternating pulses could be used. The electrical field is not necessarily pulsed and could be also continuous (dc).

One set of preferred characteristics of the electric field pulses for use according to the invention is 8 pulses applied sequentially with a time interval between each pulse of five seconds. Preferably the electric field pulse has a height of up to 1.3 kv/cm for human red blood cells, 1.6 kv/cm for rabbit red blood cells and 1.5 to 2.1 kv/cm for murine red blood cells. Preferably in one embodiment the pulse duration is at least 400$\mu$ seconds long. The pulse duration in another preferred embodiment is 1ms with a set of four pulses applied sequentially with a time interval between each pulse of 15 minutes. Preferably the pulses are square pulses. Preferably the electric field pulse is no higher than the critical electric field for electroporation of the cell.

Any isotonic medium can be used as the electro-insertion medium employed in the invention depending on the cells and the pulse generator power. In one embodiment of the invention, besides mannitol and histidine, NaCl, KCl, Na$_2$HPO$_4$, NaH$_2$PO$_4$, some carbohydrates like stachyose, inuline to any tetrasaccharide can be utilized. Physiological pH is preferred, but any pH can be used depending on the use, cells and proteins.

The electro-insertion medium for use in the present invention preferably contains in one embodiment a mixture of mannitol and histidine, preferably at a pH of 7.8. In another preferred embodiment, PBS at a pH of 8.8 is utilized.

The resealing medium for use in the present invention preferably is an aqueous medium containing one or more of KCl, NaCl, BSA, HSA, MgCl$_2$ or glucose in PBS, preferably at a pH of 7.4. MgCl$_2$ can also be used. Physiological pH is preferred for red blood cells (pH=7.4).

In a preferred embodiment of the invention, after resealing an incubation with a preservation medium, e.g., PBS or "ADSOL", is carried out at 20° to 39° C., preferably 37° C. for 1 to 2 hours, preferably 1 hour, and/or at 2 to 6° C., preferably 4° C., for 6 to 12 hours.

Figure 9:
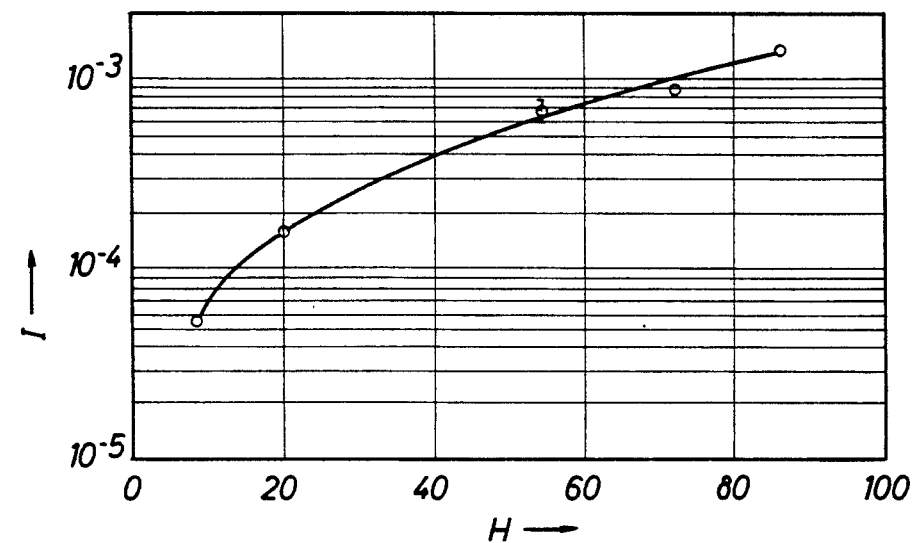
FIG. 9 is a plot showing the insertion efficiency (I=inserted protein molecules per cell/added protein molecules per cell) increases with the hematocrit. The system used was murine red blood cell-glycophorin.

The electro-insertion depends on the suspension hematocrit. FIG. 9 shows that for a constant amount of added protein molecules per red blood cell, the insertion efficiency increases with the hematocrit. Preferably the hematocrit of the solution is 0.001% to 98%. Hematocrit can be defined as the fraction of total volume occupied by red blood cells.

Figure 10:
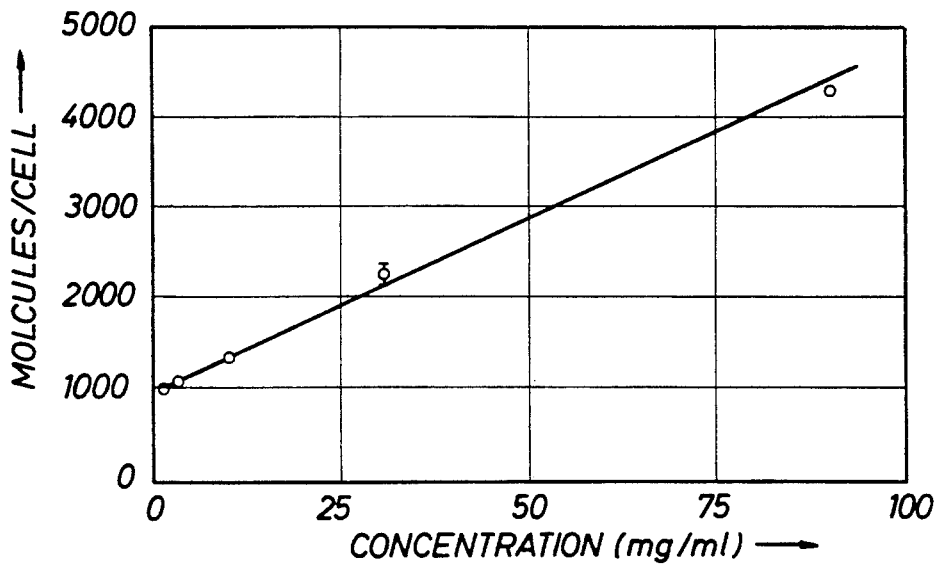
FIG. 10 is a plot depicting the number of inserted protein molecules per cell depends on the concentration of proteins. The system utilized was murine red blood cells-glycophorin.

The amount of inserted protein molecules per cell increases with the added protein concentration. Any protein concentration can be used including powder. A preferred concentration range is 0.01 mg/ml to 200 mg/ml, with 134 mg/ml being particularly preferred. FIG. 10 shows the relationship between the inserted glycophorin molecule per mouse red blood cell and the concentration of the added glycophorin at 86 hematocrit.

The hydrophobic interaction between the red blood cells membrane and the inserted protein hydrophobic sequence is a key stone of electro-insertion. The dependence of the insertion efficiency on the suspension hematocrit may be considered as a dependence on the increase of the hydrophobic phase. Moreover, the electro-insertion increases the rate of natural transfer of phosphatidyl choline nitro-beazo 7-oxa-1,3-diazole (Acyl labeled-(PCNBD) (Avanti Polar Lipids Inc., Pelham, Ala, U.S.A.) into the red blood cell membrane.

Figure 11:
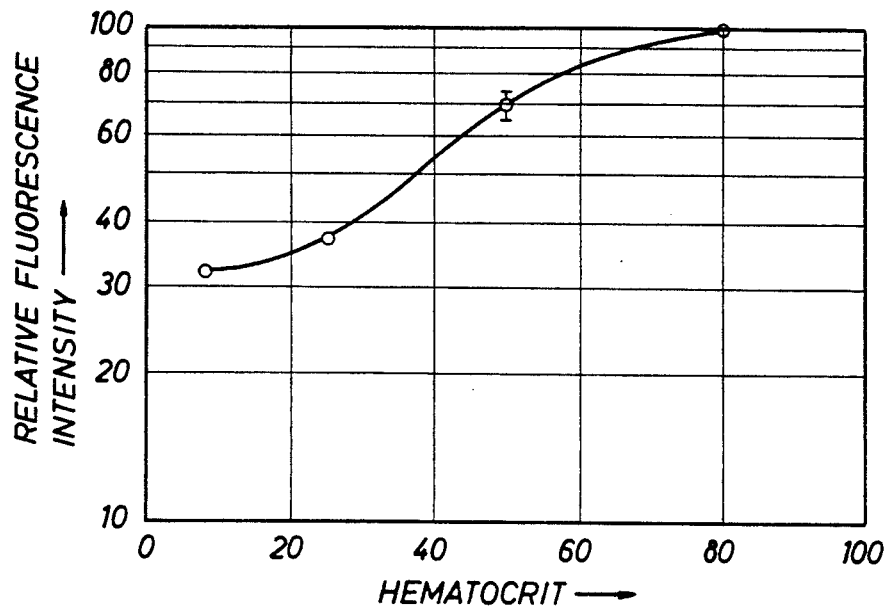
FIG. 11 is a graph showing that the insertion efficiency of PCNBD (represented as relative fluorescence intensity) depends on the hematocrit. The system used was murine red blood cells.

FIG. 11 shows the insertion efficiency as a function of hematocrit of murine red blood cells for the same amount of PCNBD. It was noticed that glycophorin (see FIG. 9) and PCNBD have similar behaviors, except that PCNBD shows higher values of insertion for lower hematocrit due the natural transfer. This similarity is further proof of the hydrophobic aspect of electro-insertion.

Moreover, it was noticed that adding L-alpha phosphatidic acid dipalmitoyl (Sigma, St. Louis, Mo., U.S.A.) improves the insertion by 35%.

Finally, proteins without hydrophobic sequence such as human $\beta_2$ microglobulin (Sigma, St. Louis, Mo., U.S.A.) were not inserted by the inventive method when detected by rabbit anti-human $\beta_2$ microglobulin antibody (Accurate Chemical and Scientific Corporation, Westbury, N.Y., U.S.A.).

A use for the present invention includes targeting of red blood cells as drug carriers, especially red blood cell-CD4+ for Acquired Immunodeficiency Syndrome (AIDS). Red blood cells bearing different proteins or antigens or antibodies as targeting elements and all applications using cell surface receptors, in cancer and in infectious diseases are also areas of use for the present invention. The product of the invention could be used as a vaccine, e.g., to treat malaria.

It is preferred that the ratio of protein molecules per cell be such that every cell is fully covered by the protein before the pulse. Depending on the state of the protein in solution (monomer or polymer), the ratio preferably is $10^6$ protein molecules per cell.

It is preferred to use a low concentration of calcium and magnesium ions, e.g., $\leq 0.5$ mM calcium and 0.5 mM magnesium for red blood cells. For other than red blood cells, the concentrations depend on the cell, because very low concentration (e.g., less than or equal to 0.5 mM) give less adsorption of protein on the cell membrane and higher concentration (for example, less than or equal to 0.5 mM) lyse cells.

Magnesium and calcium help the protein to adsorb via electrostatic interaction on the membrane of the cell. Once this happens, the protein molecule is brought closer to the membrane than it was in solution. This adsorption is optimum at the given time, and it is preferred to apply electric pulses at this time.

The invention is now described with reference to the following non-limiting examples.

EXAMPLES

EXAMPLE 1

Electro-insertion of Human Glycophorin in Murine and Rabbit Red Blood Cells

The pulse generator is a 606 Cober pulse generator. The "TEFLON" chamber used in the electro-insertion is cylindrical, 1.2 cm diameter, with each end formed by 1.2 cm×2.5 cm stainless steel electrodes, the electrodes gap is 0.2 cm. Potential and current are monitored by a Nicolet 2090 digital oscilloscope.

EXAMPLE 1a

Red cells from freshly drawn murine blood are washed three times 0.145 NaCl in PBS 7.4 buffer, and two times in the electro-insertion medium (EM) (0.3M mannitol and 6 mM histidine, pH=7.8). After addition of 0.5 mM CaCl$_2$ and 0.5 mM MgCl$_2$, the cells are incubated 5 minutes on ice and then 5 minutes at 37° C. (hematocrit 90%). Immediately after, a solution of 4 mg/ml of human glycophorin MM in 0.15 KCl and a given volume of the EM are added so that the protein concentration is 1.25 $\mu$g/$10^6$ cells. Then the suspension is incubated 5 minutes at 37° C. After this time, the suspension is centrifuged and the supernatant is removed such that the remaining hematocrit is 16%. 25 $\mu$l of this final suspension is electropulsed at 4° C., with a pulse height of 1.5 kv/cm (below the critical field for electroporation of mouse red blood cells (2.6 kv/cm). Electro-insertion is accomplished by exposing the cell suspension (25 $\mu$l) to eight successive electric field square pulses with 5 second intervals. The pulse height depends on the cell size, but its value is below the critical value for electroporation. The pulse length is 400 $\mu$s.

Then the cells are resealed for one hour at 37° C. plus one more hour in the presence of the resealing medium (RM) (1.211 g KCl, 0.9 g glucose, 0.5 g BSA, 1.02 g NaCl and phosphate buffered saline (PBS) 5 mM pH 7.4 up to 250 ml) and finally washed one time with the RM and two times in 0.145M NaCl PBS 7.4 buffer.

EXAMPLE 1b

Red cells from freshly drawn blood are washed five times in 0.14 NaCl in PBS 8.8 buffer. Membrane proteins lyophilized or suspended in 10 PBS buffer pH 8.8 are added to the red blood cells pellet (hematocrit 90%). After 20 minutes incubation on ice and 15 minutes incubation at 37° C., four electrical pulses are applied at 37° with 15 minute intervals. Each pulse is 1 ms long and 1.3 kV/cm high for human, 1.6 KV/cm for rabbit or 2.1 kV/cm for murine red blood cells. The suspension is then incubated for two more hours at 37° C. Finally, red blood cells are washed one time with plasma and two times with 5 PBS pH 7.4. Another incubation at 50% hematocrit at 37° C. in 5 PBS 7.4 or in preservation medium (the preservation medium "ADSOL" contains: 2.2 g dextrose (hydrous) USP, 900 mg sodium chloride USP, 750 mg mannitol USP and 27 mg ADENINE in 100 ml (FENWAL Laboratories, Deerfield, Ill., U.S.A.) may improve the life span of the inserted proteins into the red blood cell membranes.

EXAMPLE 2

CD4 receptor is inserted in red blood cells membrane (human, rabbit and murine) under the same conditions described in Example 1b reaching agglutinating densities when reacted with $gp_{120}$-expressing, HIV-infected H9 cells.

EXAMPLE 3

Immunofluorescence Assay

After insertion of glycophorin into the red blood cell membrane, the washed cells are then incubated with 2 μl of 0.17 mg/ml 10F7 anti-glycophorin monoclonal antibody (Biomedical Sciences Division, Livermore National Laboratory, University of California) for 30 minutes at room temperature and then washed three times 0.145M NaCl PBS 7.4 buffer. The cells are then incubated with phycoerythrin conjugated affinipure F(ab')2 fragment goat anti-mouse IgG (Jackson Immuno Research Laboratories, West Grove, Pa., U.S.A.) or fluoresceine conjugated affinipure F(ab')2 fragment rabbit anti-mouse IgG (Accurate Chemical and Scientific Corporation, Westburg, N.Y., U.S.A.) at room temperature for 30 minutes. The cells are finally washed three times in 0.145M NaCl PBS 7.4 buffer.

EXAMPLE 3a

A control sample where the murine RBC (red blood cells) have undergone all the steps mentioned in Example 1a, but without electroporation, is used as a reference.

Figure 1A:
FIG. 1a is a photograph depicting aggregation of Murine red blood cells bearing human glycoporin shown by fluorescence microscopy.

The observation of the fluorescence of the sample and the reference under the fluorescence microscope with blue light excitation shows that the cells of the control sample which has not received any electric pulse have fluorescent green points on the membrane due to the FITC fluorescence. The electroporated sample shows highly fluorescent cells which agglutinate. The agglutination is due to 10F7 Antiglycophorin bonding between cells which have integrated glycophorin. This agglutination gives an idea of the number of glycophorin molecules integrated by cell which must be of the order of $10^5$ to be able to induce agglutination of cells (see FIG. 1). The results of a pseudo ELISA confirm this order of insertions and it shows that $4.2 \times 10^5$ glycophorin per cell are inserted (see Example 6).

An explanation for the above is that the presence of $Ca^{++}$ and $Mg^{++}$ ions in low concentration (0.5 mM) in low ionic concentration medium help the glycophorin to be fixed to the plasma membrane of the red blood cell such that during the pulse the glycophorin molecules already very close to the membrane will integrate.

Figure 2A:
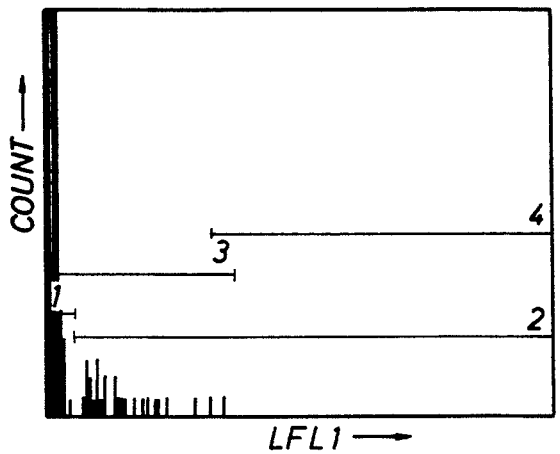
FIGS. 2a and 2b are fluorescence histograms of cell number versus fluorescence intensity obtained by cytofluorometry (EPICS PROFILE). The control sample without electric pulse (FIG. 2a) does not show any high fluorescent cells on 1213 cells counted, while the pulsed sample (FIG. 2b) shows that 10.4% of 1742 Murine red blood cells contain about $2.5 \times 10^5$ FITC corresponding to glycophorin insertion.
Figure 2B:
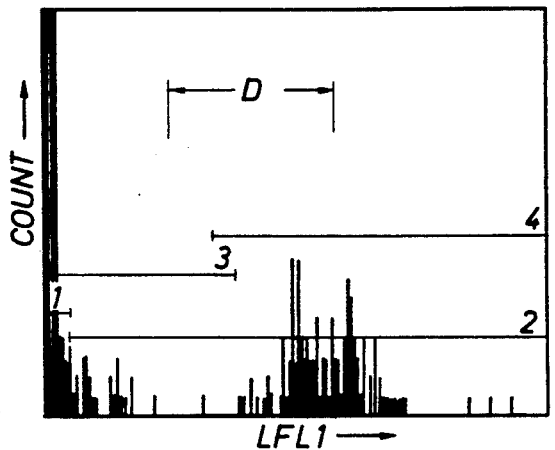

Using cytofluorimetry performed with a Coulter EPICS Profile instrument, it is difficult to ascertain a true estimation of the percentage of protein-integrated cells because of the agglutination of these cells (case of Example 1a). For some single cells, fluorescence can be measured corresponding to a mean value of $2.5 \times 10^5$ fluorescent molecule (FITC) per cell. This number is in agreement with the estimated rate of glycophorin integration necessary to induce agglutination (FIG. 2).

EXAMPLE 3b

The inserted CD4 is assayed by different anti-CD4 monoclonal antibodies including OKT4A, OKT4C and OKT4D (Ortho Diagnostic Systems, Inc., Raritan, N.J., U.S.A.), BL4/10T4 (AMAC, Inc., Westbrook, Me., U.S.A.), CYT029 (Cytogen Corp., Princeton, N.J., U.S.A.) and Leu 3A (active epitope with gp120 envelop protein of HIV virus) (Becton Dickinson Immunocytometry System, Mountain View, Calif., U.S.A.), followed by a phycoerythrin conjugated F(ab')2 fragment goat anti-mouse IgG or fluorescein conjugated affinipure F(ab')2 fragment rabbit anti-mouse IgG.

Control samples are used as references for each corresponding case, where red blood cells subjected to all the steps mentioned in Example 1b, except that glycophorin or CD4 is replaced with bovin serum albumin.

Figure 4B:
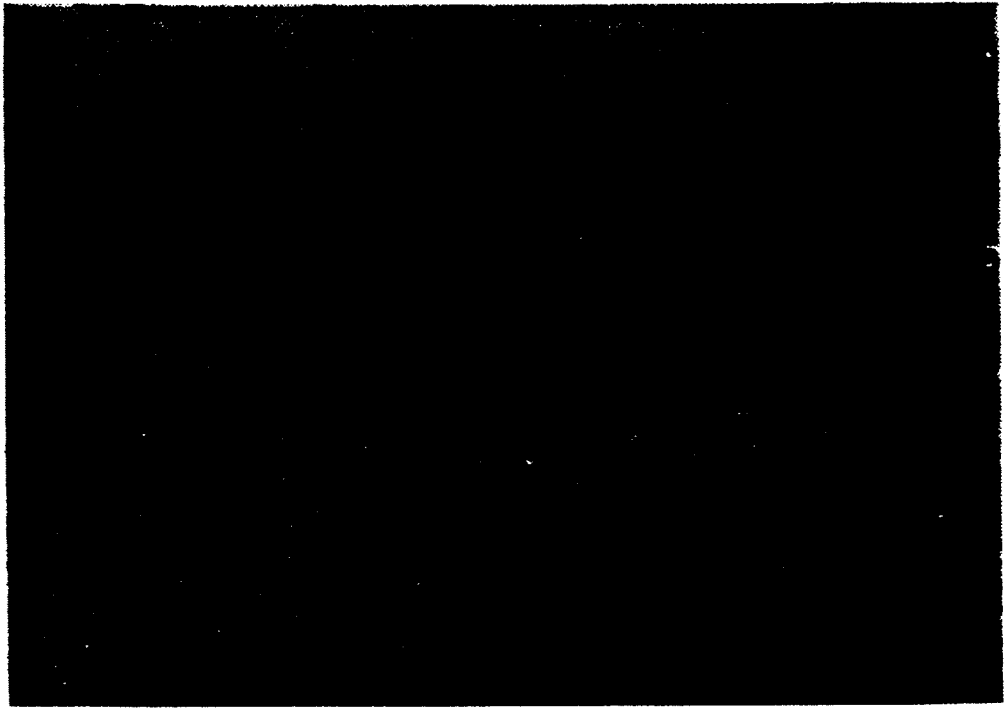
FIGS. 4a and 4b are photographs of rabbit red blood cells bearing electro-inserted human glycophorin after reaction with 10F7 anti-human glycophorin antibody and a secondary fluorescent antibody (Goat anti-mouse phycoerythrin) as it appears with fluorescence (FIG. 4a) and direct light (FIG. 4b).
Figure 4A:
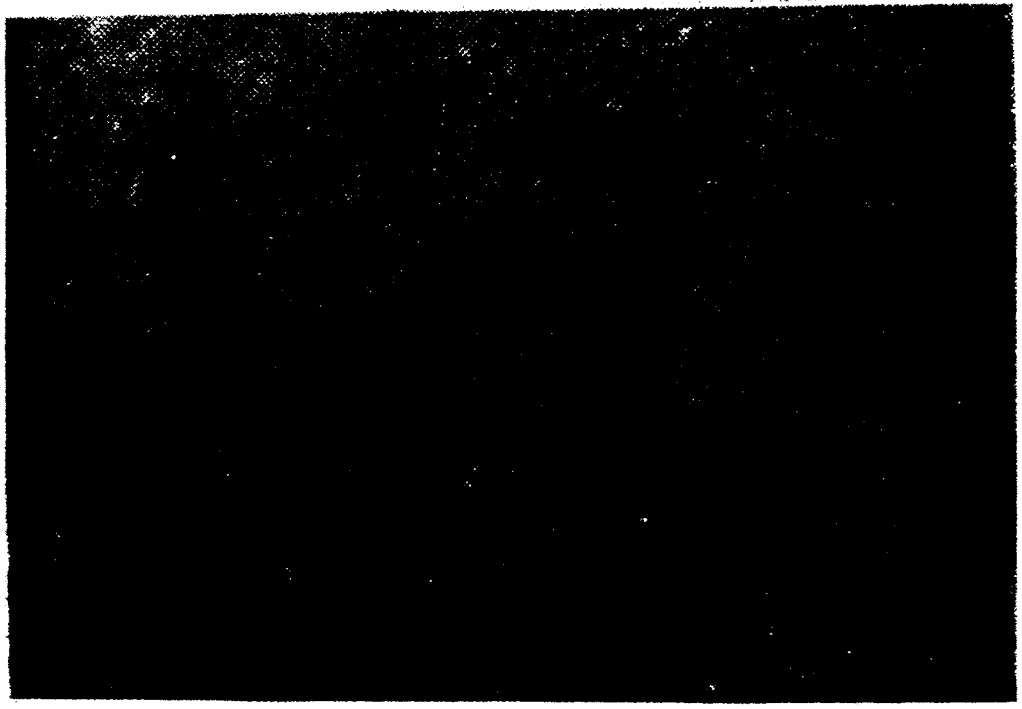
Figure 5B:
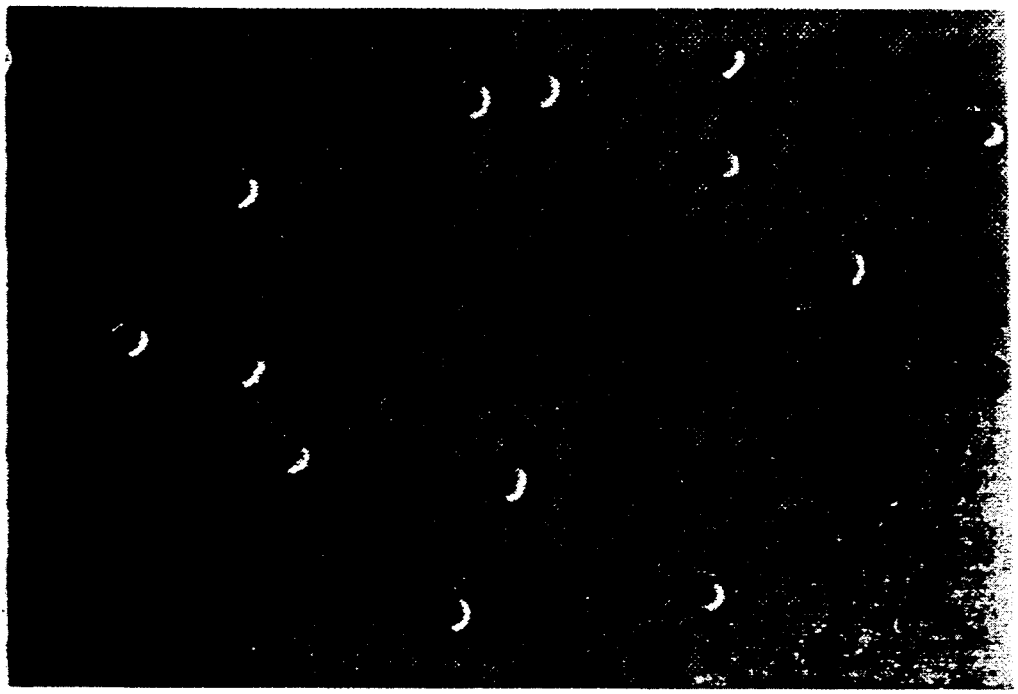
FIGS. 5a and 5b are photographs of human red blood cells bearing electro-inserted CD4 after reaction with OKT4C and Leu3a monoclonal antibodies and goat anti-mouse phycoerythrin antibody. Notice the bright fluorescent points (FIG. 5a) characteristic of the capping of the inserted proteins upon reaction with monoclonal antibodies. Under direct light (FIG. 5b) the cells appear not to be affected by the treatment.
Figure 5A:

Under the fluorescence microscope, red blood cells bearing the inserted proteins show bright fluorescent points characteristic of the capping of the inserted glycophorin (FIG. 4) into rabbit red blood cells. FIG. 5 shows detection by monoclonal antibodies fluorescently stained of CD4 electroinserted into human red blood cell membranes.

Flow cytometry was performed on a Coulter EPICS Profile instrument. The phycoerythrin was measured with a 575 nm band pass emission filter, while the fluorescein was measured with a 525 nm band pass emission filter. Alignment of the instrument was performed using 5 micrometer diameter Immunocheck beads. The high voltage of the photomultipliers was set up to obtain the characteristic fluorescence peak at the channels of these fluorescent standards, using Immunobright beads with different fluorescence intensity. The following histograms were collected for analysis: 1) 90°-sidescatter vs. forward angle scatter; 2) log green or red fluorescence vs. number of cells.

Figure 6:
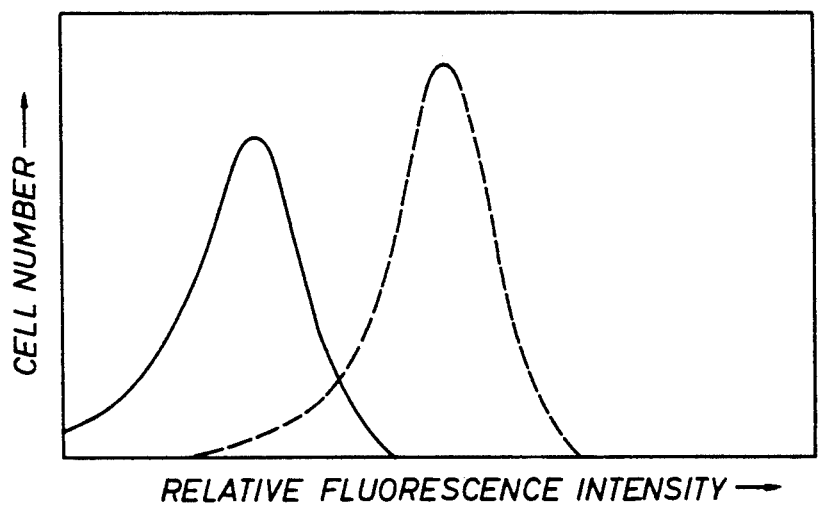
FIG. 6 is a plot which depicts the flow cytometry analysis of rabbit red blood cells-glycophorin (---), which shows a fluorescence intensity shift with respect to the control cells (—). The intensity level corresponds to 4,000 glycophorin/cell.
Figure 7:
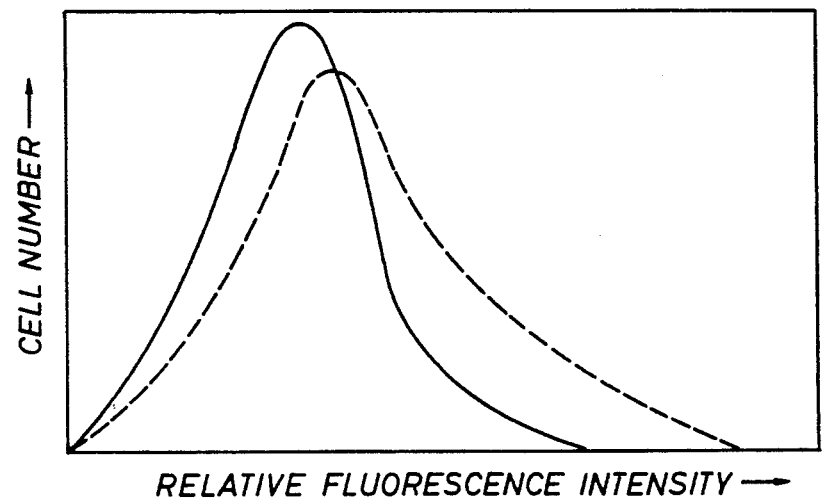
FIG. 7 is a plot which depicts the flow cytometry analysis of rabbit red blood cells CD4 (---), which shows a fluorescence intensity shift with respect to the control cells (—). The intensity level corresponds to 2,000 CD4 molecules/cell.

The flow cytometry analysis of the fluorescence intensity and the cell number shows an intensity shift of the whole population of cells with respect to the control sample. This indicates that all the red blood cells have been subjected to the electro-insertion of the xenoproteins. The mean peak channel of the fluorescence intensity is used to estimate the number of inserted protein molecules per cell. FIG. 6 represents the case of inserted glycophorin into rabbit red blood cells membrane and FIG. 7 represents the case of inserted CD4 into rabbit red blood cells membrane.

Using standard fluorescent beads (Coulter), the average number of inserted molecules per red blood cell is found to be 2000. The efficiency of insertion (inserted molecules per added molecules per cell) is 1/1000. This efficiency is underestimated because the detection of inserted molecules is made by immunofluorescence, where active epitopes are detected only, while the added number of molecules is deduced from the weight which does not represent effectively the true number of protein molecules presenting active epitopes.

EXAMPLE 4

Electro-insertion of Biotinylated Human Glycophorin in Human Red Blood Cell

Another application of the electro-insertion is the insertion of biotinylated human glycophorin in human red blood cells. The instruments and the media are the same as described above. The height of the electric field is 1.3 kv/cm, which is below the critical field for electroporation of human red blood cells (2.2 kv/cm).

EXAMPLE 5

Biotinylation of Glycophorin

Human glycophorin MN (Sigma Chemical Co., St. Louis, Mo., U.S.A.) is dissolved in sodium bicarbonate 0.1M till 0.5 mg/ml. At 4° C. and while stirring, an equal volume of 1 mg/ml succinimidyl D-biotin (molecular probes) is added drop by drop in dimethyl-formamide. The solution is incubated overnight at 4° C. with stirring. A dialysis four times with KCl 0.15M and one time with 0.3M mannitol give the glycophorin-biotin solution in mannitol used for the electro-insertion.

EXAMPLE 6

Pseudo ELISA

In order to get a quantitative evaluation of the integrated molecules of glycophorin per red blood cell, a pseudo ELISA test is used where the glycophorin-biotin molecule is labelled by alkaline phosphatase avidin (Alk. Phos. Avidin) conjugate (ICN). An ELISA plate (Costa, Cambridge, Ma., U.S.A.) is used and the color intensity is read by DYNATECH Mr 700 with a 410 nm filter.

First, a standard curve of optical density versus concentration of biotinylated glycophorin is set, and it is corrected for the background of unbiotinylated glycophorin. A serial dilution of suspended cells bearing glycophorinbiotin is made; after drying at 37° C. for 90 minutes, the cells are washed three times with a washing buffer (PBS 7.4, 1% BSA, 0.5% TWEEN 20), after the plates are blocked by adding a given volume of washing buffer and incubating 1 hour at 37° C. After three washes in the washing buffer, an alkaline phosphatase avidine diluted 1:10,000 is added and incubation is conducted for one hour at 37° C. After three washes with the washing buffer and three times with distilled water, the substrate buffer (0.4 mg/ml of para-nitrophenol phosphate in diethanolamine DEA buffer pH 9.8) is added and incubation is conducted for one hour at room temperature. Finally, reaction is stopped with 2.5N NaOH and the plates are read at 410 nM.

The counting of the number of cells per well is done by Coulter counter ZM Channelyzer 256.

A psuedo ELISA, similar to that as described above, is conducted to quantify the human glycophorin inserted in mouse red blood cells, but instead of Alk, Phos. Avidin, 10F7 antiglycophorin and Alk. Phos. AP F(ab')$_2$ fragment goat antimouse IgG is employed.

EXAMPLE 7

Electro-insertion of Glycophorin-Biotin in Plasma Membrane of Human Red Blood Cells Red cells from freshly drawn human blood are washed three times 0.145 NaCl in PBS 7.4 buffer and two times in EM. After addition of 0.5 mM of CaCl$_2$ and 0.5 mM of MgCl$_2$, the cells are incubated 5 minutes on ice and 5 minutes on 37° C. (hematocrit is 90%). Immediately, a given volume of the solution of glycophorin-biotin is added, such that 1.25 μg glycophorin per 10$^6$ cell are yielded and then incubation is conducted for five more minutes at 37° C. The suspension is then centrifuged and the supernatant removed to get a hematocrit of 16%. 25 μl of the final suspension is electropulsed at 4° C.

Immediately after the pulse, the cells are incubated at 37° C. plus one more hour in the presence of RM. Then, the cells are washed one time with the RM (see Example 1a) and two times with 0.145M NaCl PBS 7.4. Half of the sample is labelled by avidine-FITC (molecular probes) and the other half is used for ELISA.

A control sample which underwent all the steps of this example, except the electric pulse is used as reference.

Moreover, another control has been done to check for the unspecific binding of the avidin-FITC as follows: the RBC have been electroporated exactly in the same manner, but in the absence of glycophorin-biotin and the fluorescence was completely negative.

Figure 3B:
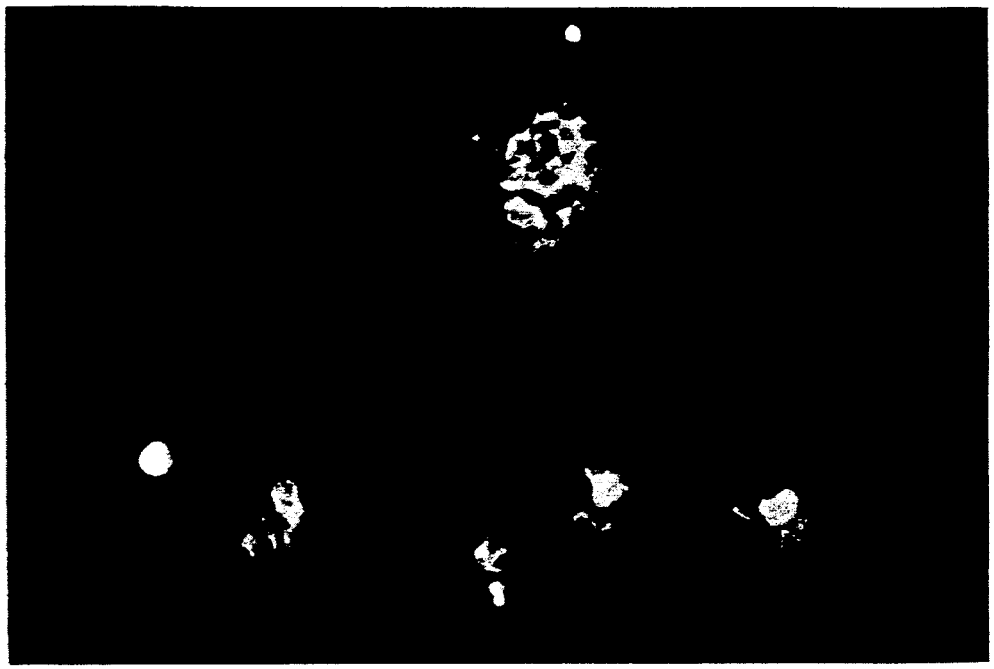
FIGS. 3a and 3b are photographs depicting agglutination of human red blood cell bearing biotinylated glycophorin as shown by white light microscope (FIG. 3a) and fluorescence microscope (FIG. 3b).
Figure 3A:
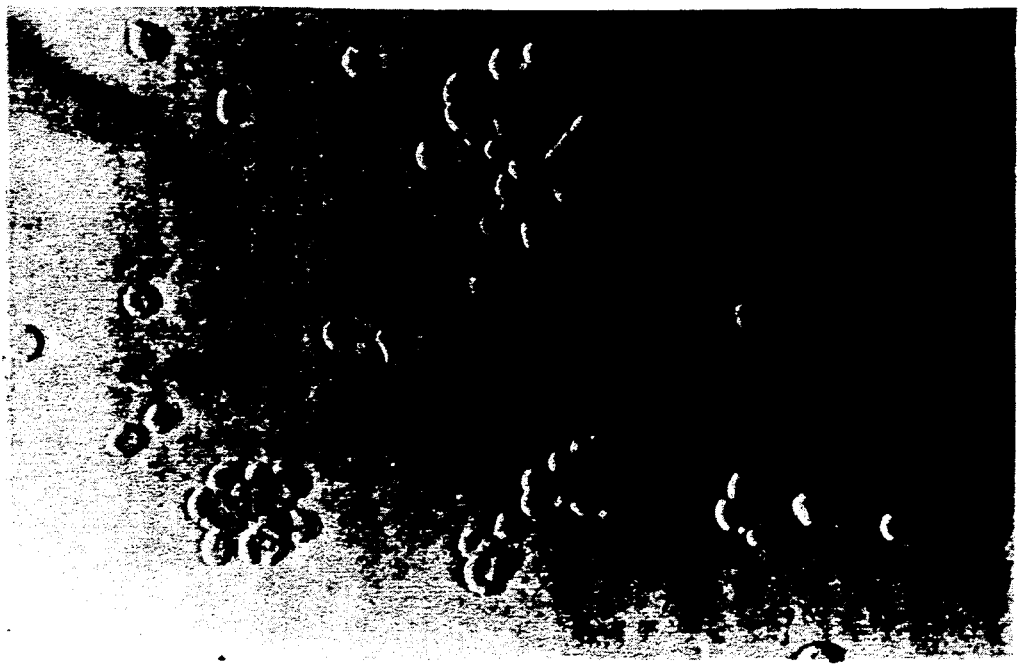

The pseudo-ELISA shows that up to $3.5 \times 10^5$ per human red blood cell can be inserted. This order of insertion is in agreement with the agglutination of the red cells bearing biotinylated glycophorin, as shown in FIGS. 3a and 3b due to cell-cell bonding by avidin. This common phenomenon of agglutination in this case and in the case of anti-glycoporin antibody is not an artefact but a strong proof of high level of insertion. The control where avidin and anti-glycophorin antibody is added on electropulsed cells does not show any agglutination. This new technique has a powerful application for the insertion of CD4 in red blood cells or the insertion of any other molecule useful for drug targeting.

EXAMPLE 8

In Vivo Life Span of $^{125}$I-Glycophorin and $^{125}$I-CD4 Inserted in Rabbit Red Blood Cells Purified rCD4 and human glycophorin were labeled with $^{125}$I using [$^{125}$I]-Bolton-Hunter Reagent ($^{125}$I-BHR) (New Research Products, Boston, Mass., U.S.A.), according to their procedure.

4 ml of blood from a male rabbit (New Zealand white 2.5 to 3 kg), obtained by auris arteriopuncture, were collected into a heparinized tube. Proteins were inserted (as explained in Example 1b) in 700 μl of packed red blood cells. After insertion, red blood cells were labeled by $^{51}$Cr using sodium chromate Cr51(Na$_2$$^{51}$CRO$_4$) kit from Mallinckrodt (Saint Louis, Mo., U.S.A.), according to their procedure. The erythrocyte-CD4+ (glycophorin+) suspension was reinfused by auris venipuncture into the same rabbit.

Figure 12:
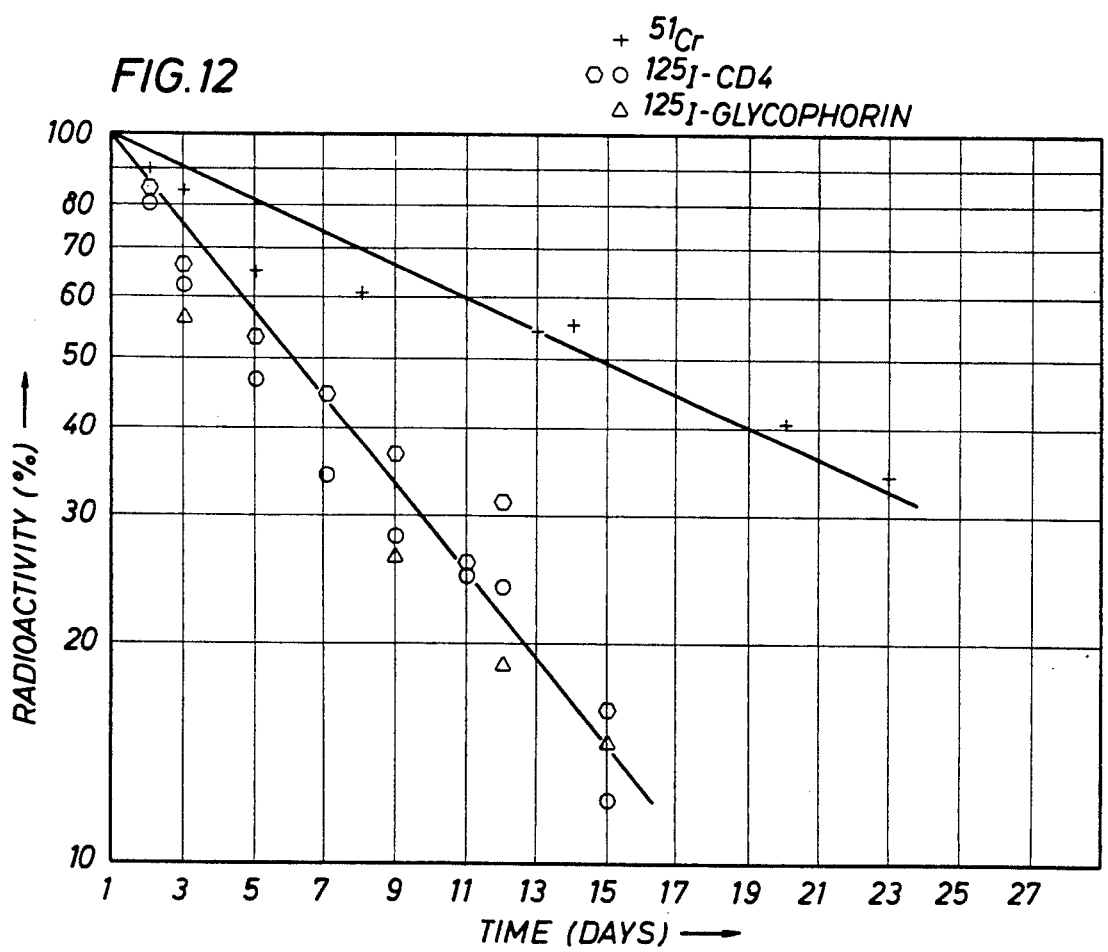
FIG. 12 is a plot showing the life span of rabbit red blood cells ($^{51}Cr$ labelled) subjected to the insertion of $^{125}I$-CD4 and $^{125}I$-glycophorin.

Blood samples (1.5 ml) were measured by an automatic gamma counting system (TM Analytic 1911 Gamma Trac from TM Analytic Inc., Elk Grove Village, Ill., U.S.A.). FIG. 12 shows the life span of the red blood cells subjected to electro-insertion and that of the inserted proteins. The chromium analysis shows that electro-insertion does not disturb the life time of the red blood cells in vivo where the half life time is 17 days. The half life time of the inserted proteins is shorter (7 days).

No immune response was detected either against inserted CD4 or glycophorin. Therefore, electro-insertion provides a long lived carrier of full length CD4 which retains its immunological activity in circulation.

CD4+ erythrocytes resuspended in autologous plasma or physiological solution (0.15M NaCl) at hematocrit 50% can be injected into the blood stream of an AIDS patient for use as a specific scavenger for free HIV virus circulating, circulating gp120 and infected cells presenting the gp120 molecule on their surface. With the latter, RBC (red blood cells)-CD4+ form aggregates which are recognized and phagocyted by the reticulo-endothelial system.

The CD4+ erythrocytes could also be loaded with a specific antiviral drug (e.g., AZT) efficient against HIV infection in order to target it to infected, phagocytic cells.

The electro-insertion process according to the invention could be used to insert other membrane proteins into the erythrocyte membrane in order to treat other diseases involving specific surface antigens or receptors, e.g., hepatitis B virus and malaria, or where targeting drug delivery by means of red blood cells with electro-inserted membrane proteins is desired.

The present invention can also be employed to treat autoimmune diseases by electro-inserting appropriate antibodies in red blood cell membranes and then administering such red blood cell membranes to patients.

EXAMPLE 9

Electro-Insertion of Glycophorin Into CEM Cell Membrane

The electro-insertion of human glycophorin into human lymphoma T cells (CEM) cell membrane is accomplished using the same procedure described above for red blood cells. About 1000 glycophorin molecules per CEM cell have been detected. This result shows that electro-insertion technique can be applied to eukaryotic, nucleated cells as well.

EXAMPLE 10

Spontaneous Insertion of Glycophorin and CD4 Into Murine, Rabbit and Human Red Blood Cell Membrane Red cells from freshly drawn blood are washed five times in 0.14 NaCl in PBS 8.8 buffer. Membrane proteins (glycophorin or CD4) lyophilized or suspended in 10 PBS pH 8.8 are added to the red blood cells pellet (hematocrit 90%). After 20 minutes incubation on ice and 3 hours incubation at 37° C., red blood cells are washed one time with plasma and two times with 5 PBS pH 7.4. Depending on the added protein concentration, up to 4500 epitopes are detected by an immunofluorescence assay using flow cytometry analysis.

It will be appreciated that the instant specification and claims are set forth by way of illustration and not limitation, and that various modifications and changes may be made without departing from the spirit and scope of the present invention.

What is claimed is:

1. A method for incorporating a human CD4 or human glycophorin protein into the membrane of a red blood cell, comprising exposing the red blood cell to an electric field the height of which is at or below about the critical field for electroporation while said cell is suspended in an electro-insertion medium in the presence of a solution of 10 mM phosphate buffered saline at a pH of 8.8, and CD4 or glycophorin, said CD4 or glycophorin bearing a hydrophobic membrane spanning sequence, and then resealing by contacting the resultant cell with a resealing medium.

2. A method according to claim 1, wherein the electric field comprises one or more electric field pulses.

3. A method according to claim 2, wherein the height of the electric field pulse critical field for electroporation, is calculated using the formula:

$$V = V_o + 1.5\ R\ E \cos(\Theta),$$

where V is the resultant membrane potential, $V_o$ is the natural membrane potential, R is the cell radius, E is the field strength, and $\Theta$ is the angle between a given membrane site and the field direction.

4. A method according to claim 2, wherein the electric field pulse is 400 $\mu$s to 1 ms long.

5. A method according to claim 2, wherein the electric field pulse is a square pulse.

6. A method according to claim 2, wherein the electric field pulses comprises up to four electric pulses applied sequentially with 15 minute time intervals between each pulse.

7. A method according to claim 2, wherein the pulse height is 1.3 kv/cm to 2.1 kv/cm.

8. A method according to claim 1, wherein the resealing medium is an isotonic medium.

9. A method according to claim 8, wherein the resealing medium comprises an aqueous mixture of 1.211 g KCl, 0.9 g glucose, 0.5 g BSA and 1.02 NaCl made up to 250 ml with 5 mM, pH 7.4 phosphate buffer.

10. A method according to claim 1, wherein the red blood cell suspension has a hematocrit of 0.001% to 98%.

11. A method according to claim 1, wherein the method is conducted at a temperature of 2° C. to 39° C.

12. A method according to claim 1, wherein the method is conducted for a time of 1 to 4 hours.

13. A method according to claim 1, wherein the method is conducted at a temperature of 37° C. and the method is conducted for a time of 3 hours.

14. A method according to claim 1, wherein the solution further comprises L-alpha-phosphatidic acid dipalmitoyl.

15. A method according to claim 1, which further comprises incubating conducted at a temperature of 20° C. to 39° C. for 1 to 2 hours in a preservative medium after resealing.

16. A method according to claim 1, which further comprises incubating at a temperature of 2° to 6° C. for 6 to 12 hours in a preservative medium after resealing.

* * * * *